(12) United States Patent
Seo et al.

(10) Patent No.: US 7,727,238 B2
(45) Date of Patent: Jun. 1, 2010

(54) DETERMINATION DEVICE FOR SIZE OF CUTTING BLOCK USING CONNECTION DEVICE

(75) Inventors: Jai-Gon Seo, Seoul (KR); Chong-Bum Kim, Goyang (KR)

(73) Assignee: Incheon University Industry Academic Cooperation Foundation, Incheon (KR)

(*) Notice: Subject to any disclaimer, the term of this patent is extended or adjusted under 35 U.S.C. 154(b) by 697 days.

(21) Appl. No.: 10/545,534

(22) PCT Filed: Mar. 27, 2004

(86) PCT No.: PCT/KR2004/000703
§ 371 (c)(1),
(2), (4) Date: Aug. 12, 2005

(87) PCT Pub. No.: WO2004/084741
PCT Pub. Date: Oct. 7, 2004

(65) Prior Publication Data
US 2006/0217732 A1    Sep. 28, 2006

(30) Foreign Application Priority Data
Mar. 27, 2003   (KR) ................... 10-2003-0019321

(51) Int. Cl.
*A61B 17/58* (2006.01)
(52) U.S. Cl. ................. 606/88; 606/87; 606/102
(58) Field of Classification Search ........... 606/87, 606/88, 89, 79, 102, 86 R, 90; *A61B 17/58*
See application file for complete search history.

(56) References Cited
U.S. PATENT DOCUMENTS
4,487,203 A    12/1984   Androphy 4,567,886 A  *  2/1986   Petersen ................. 606/88

(Continued)

OTHER PUBLICATIONS

John T. Andronico, MD et al: "The Series 7000 Total Knee System" (Passport) Nov. 1996, Femoral Sizing, p. 16.

*Primary Examiner*—Eduardo C Robert
*Assistant Examiner*—Jan Christopher Merene
(74) *Attorney, Agent, or Firm*—John K. Park; Park Law Firm

(57) ABSTRACT

Disclosed is a determination device for the size of a cutting block. The determination device includes the connection device mounted to a tibia to be placed at a top surface thereof along an upper line of a predetermined flexion gap; a body including a slide groove on a central portion of a front surface thereof, a bent part on an upper portion thereof to be placed at a precut anterior cortex of a femur, and a plurality of graduations provided on the body to determine the size of the cutting block; a slider to be slidably engaged with the slide groove of the body and including an indicating line on an upper portion thereof, and a guide to be assembled with the slider and come into surface contact with the top surface of the connection device at a lower portion thereof. The conventional devices are problematic in terms of being incapable of determining a cutting block suitable for the damaged state of a knee joint of a patient because the size of the cutting block is determined by measuring only the height of the femur with no consideration of a flexion gap. The problem encountered in the prior art can be overcome by using the determination device for the size of the cutting block according to the present invention.

6 Claims, 5 Drawing Sheets

U.S. PATENT DOCUMENTS

| | | | |
|---|---|---|---|
| 4,759,350 A * | 7/1988 | Dunn et al. | 606/82 |
| 5,049,149 A | 9/1991 | Schmidt | |
| 5,133,758 A | 7/1992 | Hollister | |
| 5,213,112 A | 5/1993 | Niwa | |
| 5,364,401 A * | 11/1994 | Ferrante et al. | 606/84 |
| 5,486,178 A * | 1/1996 | Hodge | 606/82 |
| 5,562,675 A | 10/1996 | McNulty et al. | |
| 5,597,379 A | 1/1997 | Haines | |
| 5,662,656 A * | 9/1997 | White | 606/88 |
| 5,776,137 A * | 7/1998 | Katz | 606/88 |
| 5,935,132 A * | 8/1999 | Bettuchi et al. | 606/87 |
| 6,024,746 A * | 2/2000 | Katz | 606/88 |
| 6,458,135 B1 * | 10/2002 | Harwin et al. | 606/88 |
| 2007/0118138 A1 * | 5/2007 | Seo et al. | 606/87 |
| 2007/0173851 A1 * | 7/2007 | McMillen et al. | 606/87 |
| 2008/0097450 A1 * | 4/2008 | Brown et al. | 606/88 |
| 2008/0140081 A1 * | 6/2008 | Heavener et al. | 606/87 |
| 2008/0195110 A1 * | 8/2008 | Plassy et al. | 606/88 |

* cited by examiner

DETERMINATION DEVICE FOR SIZE OF CUTTING BLOCK USING CONNECTION DEVICE

TECHNICAL FIELD

The present invention relates, in general, to a determination device for the size of a cutting block using a connection device. More particularly, the present invention relates to a determination device for the size of a cutting block used to determine the size of a cutting block which determines the standard size of an artificial joint to replace a worn, damaged or diseased knee joint upon knee arthroplasty, using a connection device as described in Korean Pat No. 10-399489 or an equivalent thereof.

BACKGROUND ART

Knee arthroplasty has become one of the most commonly performed surgeries, with which a damaged or deformed knee joint due to congenital deformation, traumatic injuries, diseases, degenerative arthritis, etc. is removed and replaced with an artificial joint. In brief, referring to FIG. 1, the anterior cortex 15 is first cut according to the damaged or deformed state of a knee joint of a patient. And, an extension gap is determined to allow for bone cutting matching with the size of an artificial joint (prosthesis). The femur 10 is undercut according to the extension gap. In addition, according to the determined extension gap, referring to FIG. 2, a flexion gap is determined based on an upper end of the tibia 20. Then, referring to FIG. 3, the posterior condyles 11, the posterior chamfer 12, the anterior cortex 13 and the anterior chamfer 14 of the femur 10 are cut using an appropriate femoral cutting block 30. An artificial joint is then implanted to replace the cut knee joint.

The flexion gap, which is required for the knee to be flexed from an extended (straight) position, indicates the gap between the cut surface of the upper end of the tibia 20 and the cut surface of the posterior femoral condyles 11. Since the femur and the tibia rotate at a state of being in close contact with each other, the flexion gap is typically determined to be identical to the extension gap. However, the flexion gap may be determined according to 3-D shape of the damaged knee joint of a patient.

On the other hand, the femoral cutting block 30, used upon the posterior and anterior cuts at the posterior condyles 11, the posterior chamfer 12, the anterior cortex 13 and the anterior chamfer 14 of the femur 10, is commercially available in a standardized size corresponding to the size of the flexion gap. Therefore, the femoral cutting block 30 is determined to have a size corresponding to that of the determined flexion gap, while the size of the artificial joint is determined according to the size of the femoral cutting block.

However, conventional devices for determining the size of a cutting block are problematic in terms of being incapable of determining a cutting block with a proper size because the size of the cutting block is determined by measuring only the height of the femur without any consideration for the size of a flexion gap that varies depending on the size of the cutting block.

Referring to FIG. 4, the problem of the conventional devices for determining the size of the cutting block will be described in detail, as follows. A conventional device 40 for determining the size of the cutting block includes a support 41 to be placed at the posterior femoral condyles 11 and a bar 42 to be placed at the anterior femoral cortex 15. The bar 42 is slidably connected with the support 41 and has a predetermined number of graduations. The support 41 includes an indicating line. A graduation of the bar is determined, which is aligned with the indicating line of the support 42, by closely contacting the support 41 and the bar 42 with the position femoral condyles 11 and the anterior femoral cortex 15, respectively. The measured graduation becomes to the size of a cutting block 30, and thereby the size of an artificial joint is determined.

However, there is a significant problem experienced in this conventional device 40 for determining the size of the cutting block. That is, the graduation of the bar indicated by the indicating line is changed by the damaged or deformed state of the posterior femoral condyles, by the cut degree of the anterior femoral cortex or by the total height of the femur, thereby the size of the cutting block is varied.

As described above, the flexion gap is the gap between the cut surface of the upper end of the tibia 20 and the cut surface of the posterior femoral condyles 11, and the size of the cutting block should be determined by the flexion gap. However, since the conventional devices determine the size of the cutting block by only the height of the femur without any consideration of the flexion gap, the devices have the problem of being incapable of determining the cutting block with a proper size to allow a surgeon to perform a bone cutting operation to define a desired flexion gap.

If a cutting block with an unsuitable size is determined, a determined artificial joint has also an unsuitable size. This unsuitable prosthesis results in a limitation in normal physical behavior. Consequentially, extension and flexion exercises of the knee are not normal, and an imbalance occurs between the muscle and the ligament that constitute the knee joint.

DISCLOSURE OF THE INVENTION

The present invention has been made keeping in mind the above problems occurring in the prior art, and an object of the present invention is to provide a determination device for the size of a cutting block using a connection device as described in Korean Pat. No. 10-399489 or an equivalent thereof.

In order to accomplish the above object, the present invention provides a determination device for the size of a cutting block using a connection device, including the connection device mounted to a tibia to be placed at a top surface thereof along an upper line of a predetermined flexion gap; a body including a slide groove on a central portion of a front surface thereof, a bent part on an upper portion thereof to be placed at a precut anterior cortex of a femur, and a plurality of graduations provided on the body to determine the size of the cutting block; a slider to be slidably engaged with the slide groove of the body and including an indicating line on an upper portion thereof; and a guide to be connected with the slider and come into surface contact with the top surface of the connection device at a lower portion thereof.

The aforementioned object of the present invention will be more clearly understood from the following detailed description taken in conjunction with the accompanying drawings.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 5:
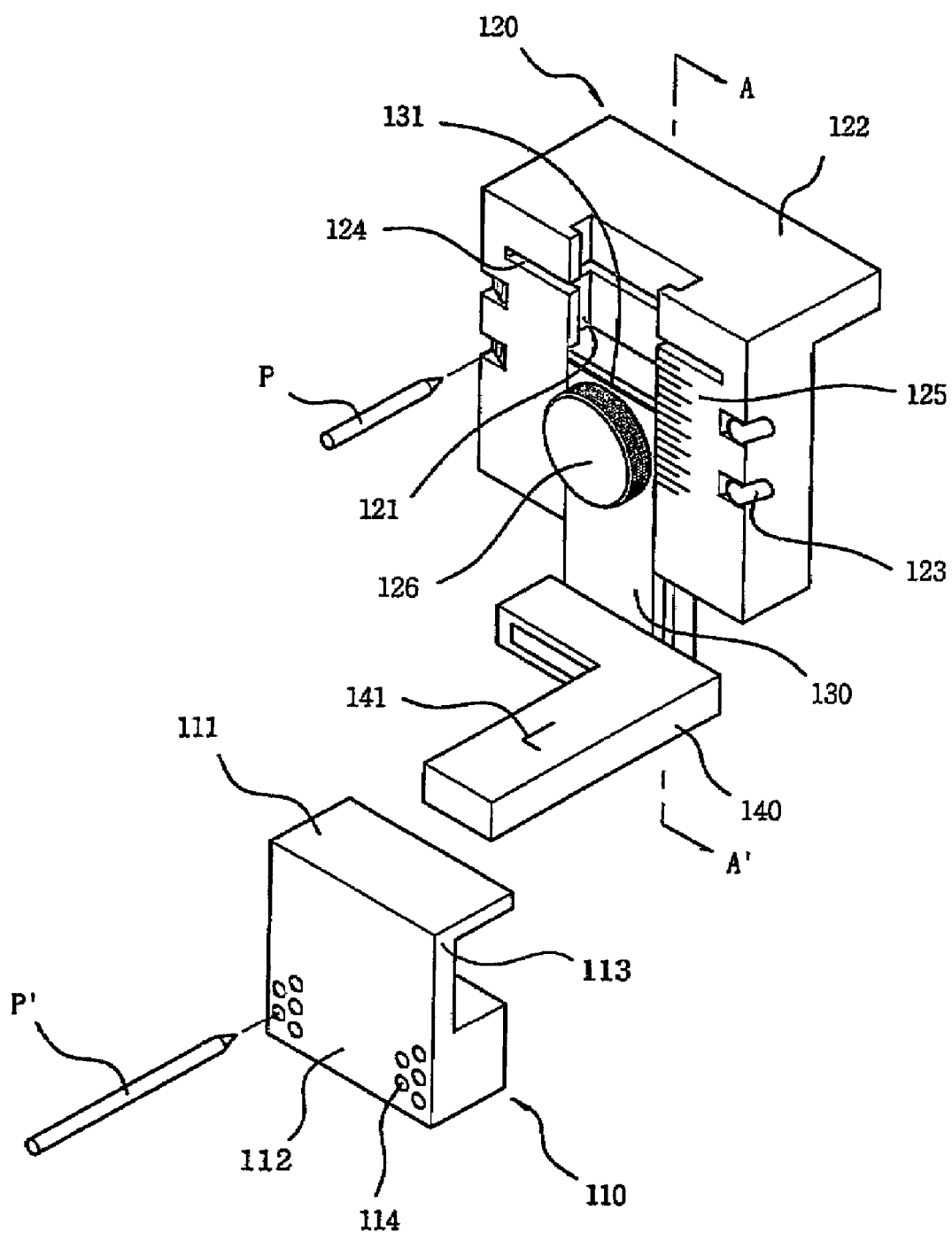
FIG. 5 is a perspective view of a determination device for the size of a cutting block according to the present invention.

With reference to the accompanying drawings, an embodiment of the present invention will be described in detail. Referring to FIG. 5, a determination device 100 for the size of a cutting block includes a connection device 110, a body 120, a slider 130 and a guide 140.

The connection device 110 may be a connection device as described in Korean Pat. No. 10-399489 or an equivalent thereof. The connection device 110 includes a supporting part 111 on an upper portion thereof, a fixation part 112 on a lower portion thereof and a side plate 113. In the connection device 110, the support part 111 is integrated with the fixation part 112 into a single body by the side plate 113. A plurality of pin holes 114 are provided on the fixation part 112 at regular intervals.

The body 120 has a quadrilateral shape, and is formed with a slide groove 121 on a central portion of a front surface thereof, and with a bent part 122 on an upper portion thereof. A slider 130, which will be described in detail below, is slidably engaged with the slide groove 121. The bent part 122 is safely placed at the precut posterior cortex 15 of the femur. In addition, preferably, a plurality of inclined pin holes 123 are formed on a side surface of the body 120. The body 120 may be fixed to the femur by a Pin P passing through each of the pin holes 123 and by being inserted into the femur. Since the body may be fixed to the femur, it is possible to correctly measure the size of the femur. Further, a plurality of graduations 125 are provided on a front surface of the body 120, which correspond to the sizes of commercially available cutting blocks. Preferably, an additional bone cutting crevice 124 is provided on the upper portion of the body 120 to execute an additional cutting of the anterior femoral cortex. If necessary, the anterior femoral cortex 15 may be further cut by inserting a vibratory saw into the cutting crevice 124.

Figure 6:
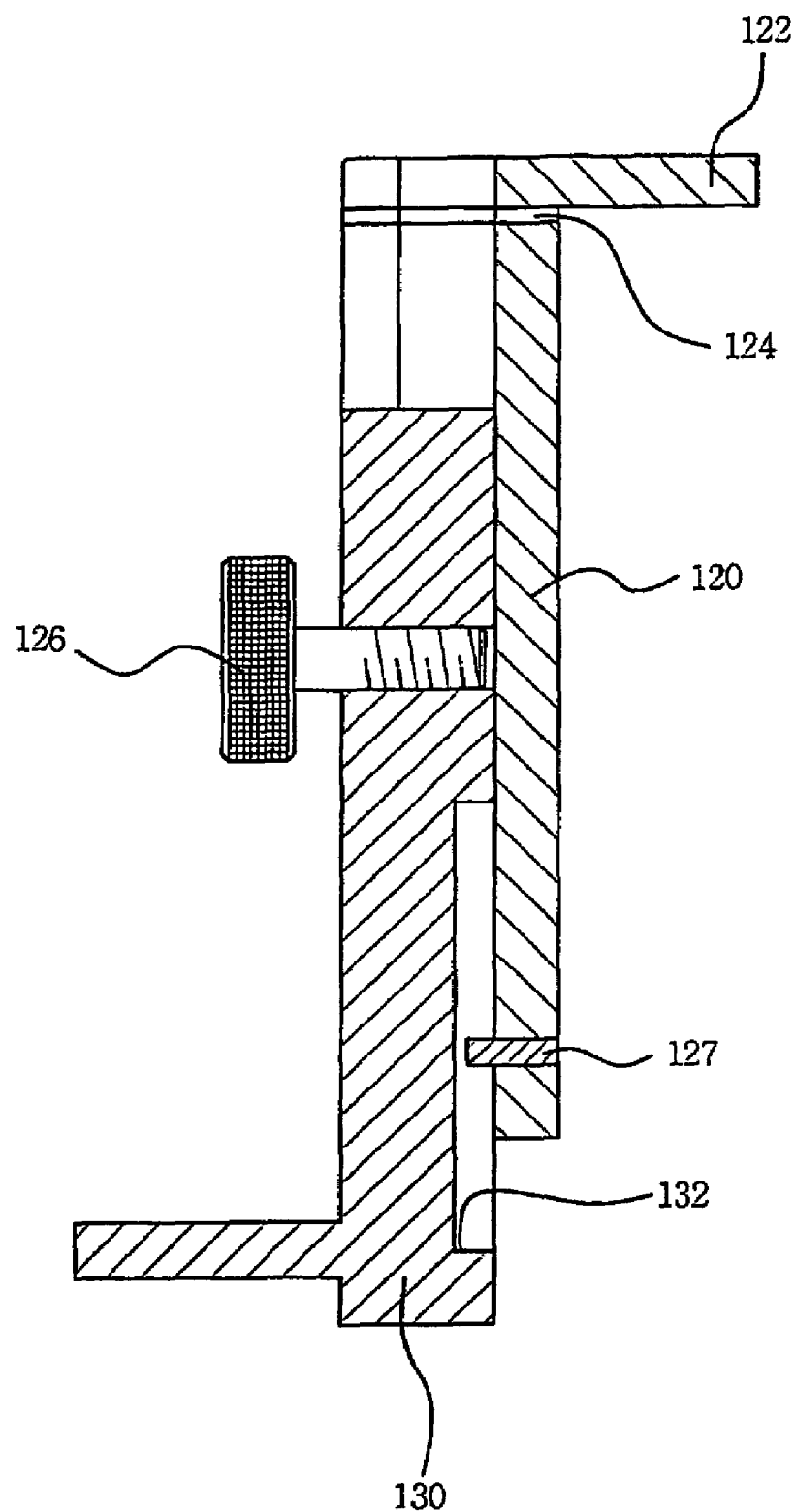
FIG. 6 is a sectional view taken along the line A-A' of FIG. 5.

The slider 130 is slidably engaged with the slide groove 121 of the body 120, and includes an indicating line 131 on an upper portion thereof to measure a graduation of the body 120. Preferably, as shown in FIG. 6, a guide groove 132 is provided in a vertical direction on a rear surface of the slider 130. A protruding pin 127 is forcibly inserted into the body 120 from the rear surface of the body 120 to be guided along the guide groove 132. By this protruding pin 127, the body 120 and the slider 130 are not separated from each other. In addition, a locking bolt 126 is preferably provided on a front surface of the slider 130 to fix the slider 130 to a predetermined position of the body 120.

The guide 140 is connected with the slider 130 and comes into surface contact with the top surface of the connection device 110 at a lower portion thereof. Also, the guide 140 is marked with a sign (141), which includes an L (Left) or R (Right) sign, to be applicable to both right and left knee arthroplasties by being reversibly inserted into the slider 130. Preferably, the guide and the slide are interconnected by a check ball (not shown).

Figure 7:
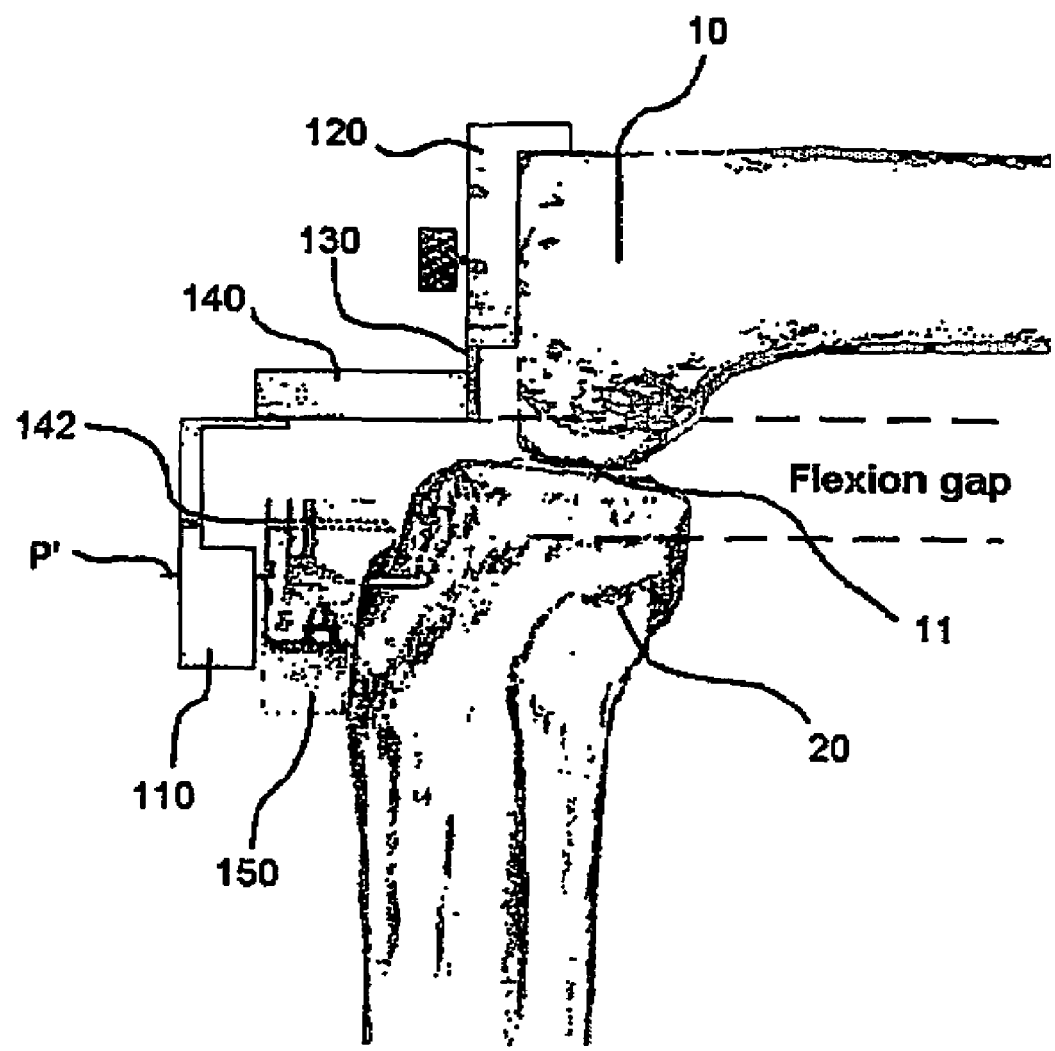
FIG. 7 is a view showing application of the determination device of the present invention to a flexed knee joint so as to determine the size of a cutting block.

Referring to FIG. 7, the practical application of the determination device for the size of the cutting block according to the present invention will be described below.

Figure 1:
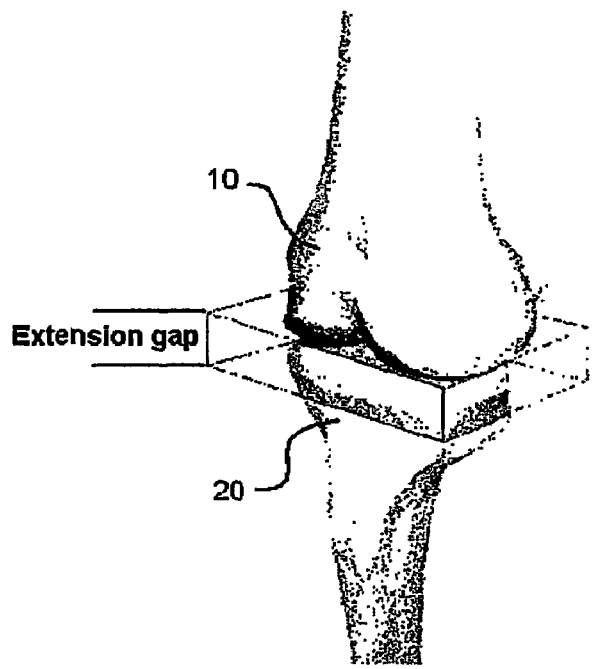
FIG. 1 is a view showing an extension gap.
Figure 2:
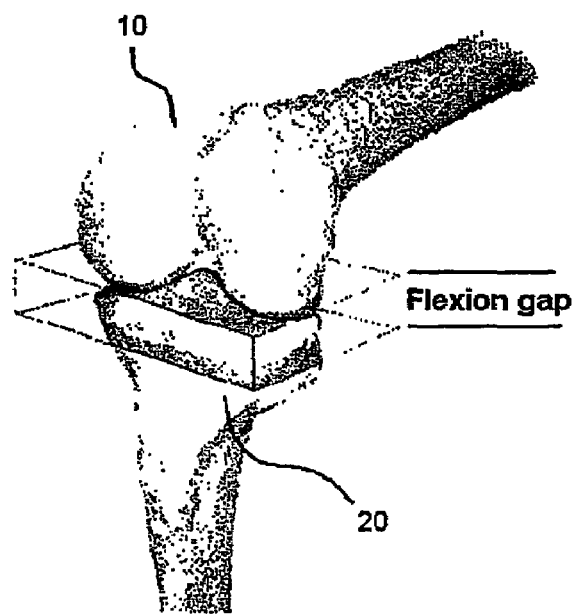
FIG. 2 is a view showing a flexion gap.

First, an extension gap as shown in FIG. 1 is measured according to the damaged or deformed state of a knee joint of a patient, and a flexion gap is determined depending on the measured extension gap. The flexion gap is typically determined to be identical to the extension gap, but is often determined just by experience of a surgeon based on a difference in 3-D shape of the knee joint between a healthy person and the patient.

Two pins (P') are respectively inserted through two he pin holes 114 each provided at each of the right and left locations of the connection device 110 matching to the measured extension gap, thus being driven into a tibia 20. The connection device 110 is then removed from the knee joint. Thereafter, a bone cutter 150 for the top-cutting of the tibia 20 is inserted into the two pins (P') driven in the tibia 20. Thereafter, the connection device 110 is again inserted into the two pins (P') to position the bottom surface of the flexion gap on the same line as the bone cutting crevice 142 of the bone cutter 150 and to position the top surface of the flexion gap on the top surface of the support part 111 of the connection device 110.

Subsequently, the determination device for the size of the cutting block according to the present invention is placed on the femur 10 of the knee at a flexion position. As a result, the bent part 122 of the body 120 is placed at a precut anterior cortex 50 of the femur 10, while the guide 140, on a lower surface thereof, comes into surface contact with the top surface of the connection device 110. Then, the slider 130 connected with the guide 140 slides along the slide groove 121 of the body 120.

Figure 3:
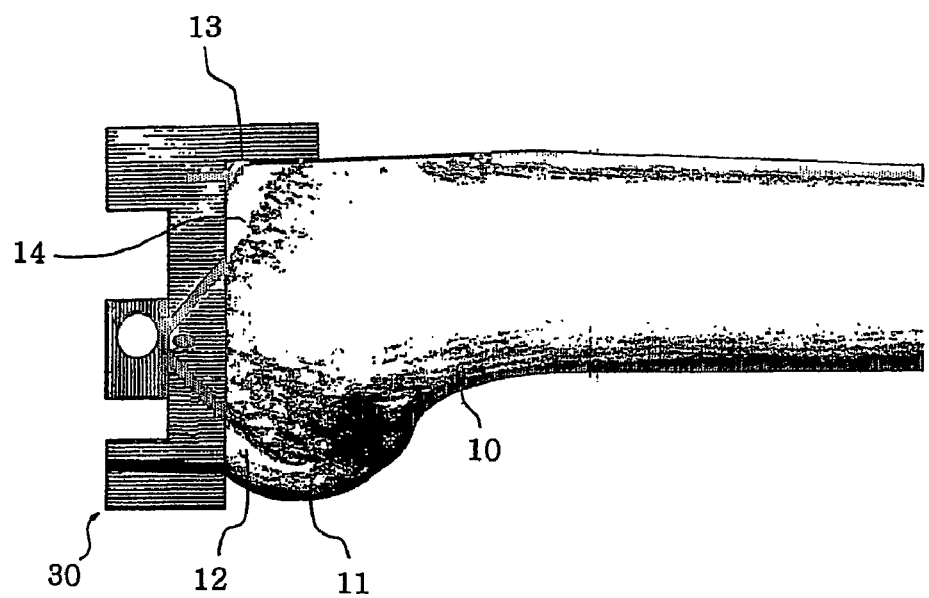
FIG. 3 is a view showing a cutting block.

When the slider 130 is stopped, one graduation of the body 120 indicated by the indicating line 131 of the slider 130 is checked among the plurality of graduations 125 of the body 120. The measured graduation designates the size of a cutting block for cuts at the posterior condyles 11, the posterior chamfer 12, the anterior cortex 13 and the anterior chamfer 14 of the femur 10, which are shown in FIG. 3, and designates the size of an artificial joint as a replacement for the damaged knee joint.

Figure 4:
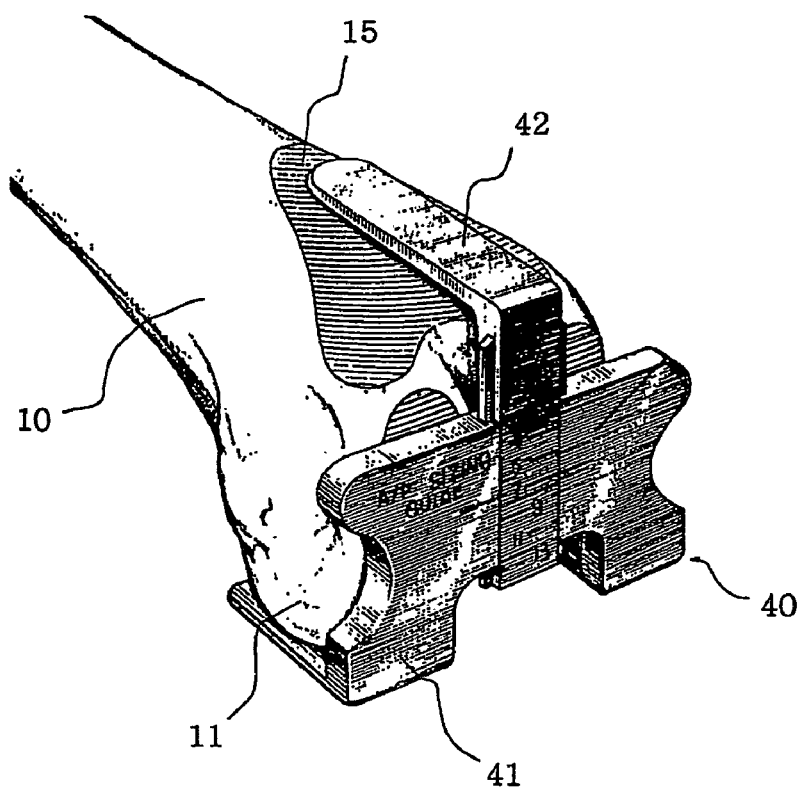
FIG. 4 is a perspective view of a conventional device for determining the size of a cutting block.

If necessary, the body 120 may be fixed to the femur 10 via the pin (P). Furthermore, the anterior cortex 15 of the femur 10, which is shown in FIG. 4, may be additionally cut via the additional bone cutting crevice 124. Also, the slider 130 may be fixed to the body 120 by the locking bolt 126. The guide 140 may be applicable to both right and left knee arthroplasties by being reversibly inserted into the slider 130. Furthermore, the slider 130 and the guide 140 may be integrated into a single body.

INDUSTRIAL APPLICABILITY

As described hereinbefore, the determination device for the size of a cutting block according to the present invention allows for the determination of a cutting block with a size matching to a determined flexion gap. Therefore, the present determination device is advantageous in terms of facilitating the selection of an artificial joint securing a normal physical behavior of a patient and thus allowing the patient to perform active extension and flexion exercises of the knee after knee joint replacement.

What is claimed is:

1. A determination device for a size of a cutting block, comprising:
    a connection device, comprising a supporting part having a flat top surface on an upper portion thereof,
a fixation part on a lower portion thereof,
a side plate,
a plurality of holes formed on the fixation part,
and a plurality of pins to be inserted through the holes for placing the flat top surface of the supporting part on an upper line of a predetermined flexion gap, the connection device is adapted to be fixed to a tibia by driving at least two of the plurality of pins through corresponding holes into the tibia;
a body including a slide groove formed on a central portion of a front surface thereof, a bent part formed on an upper portion for safely mounting a precut anterior cortex of a femur on the bent part, and a plurality of graduations provided on the body to determine the size of the cutting block;
a slider slidably connected with the slide groove of the body and including an indicating line on an upper portion thereof; and
a guide, adapted to be placed on a femur, including an end fixed to the slider and a flat bottom surface of the guide coming into surface contact with the flat top surface of the supporting part of the connection device so as to stop a sliding movement of the slider and to place the flat bottom surface of the guide on the upper line of the predetermined flexion gap wherein the slider is placed so that length directions of the slider and the femur are perpendicular or substantially perpendicular, wherein the guide is marked with right and left directions to be applicable to both right and left knee arthroplasties by being reversibly inserted to the slider.

2. The determination device of claim 1, wherein the body, on a side surface thereof, has a plurality of pin holes through each of which a pin passes.

3. The determination device of claim 1, further comprising a locking bolt to fix the slider to the body.

4. The determination device of claim 1, wherein the slider comprises a guide groove formed in a vertical direction on a rear surface of the slider, and the body comprises a protruding pin forcibly inserted into the body from a rear surface of the body to be guided along the guide groove.

5. The determination device of claim 1, wherein the body comprises an additional bone cutting crevice formed on an upper portion thereof to execute an additional cutting of the anterior femoral cortex.

6. The determination device of claim 1, wherein the slider and the guide are integrated into a single body.

* * * * *